(12) United States Patent
Leysieffer

(10) Patent No.: US 6,334,072 B1
(45) Date of Patent: *Dec. 25, 2001

(54) FULLY IMPLANTABLE HEARING SYSTEM WITH TELEMETRIC SENSOR TESTING

(75) Inventor: Hans Leysieffer, Taufkirchen (DE)

(73) Assignee: Implex Aktiengesellschaft Hearing Technology, Ismaning (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/369,184

(22) Filed: Aug. 6, 1999

(30) Foreign Application Priority Data

Apr. 1, 1999 (DE) .............................. 199 14 993

(51) Int. Cl.[7] .............................. A61F 11/04; H04R 25/00
(52) U.S. Cl. .............................................. 607/57
(58) Field of Search ................ 607/55–57, 136–137; 600/25, 559; 623/10

(56) References Cited

U.S. PATENT DOCUMENTS

| | | |
|---|---|---|
| 4,729,366 | 3/1988 | Schaefer . |
| 4,850,962 | 7/1989 | Schaefer . |
| 5,015,225 | 5/1991 | Hough et al. . |
| 5,170,434 | 12/1992 | Anderson ................ 381/68 |
| 5,277,694 | 1/1994 | Leysieffer et al. . |
| 5,279,292 | 1/1994 | Baumann et al. . |
| 5,498,226 | 3/1996 | Lenkauskas . |
| 5,554,096 | 9/1996 | Ball . |
| 5,584,869 | 12/1996 | Heck et al. ................ 607/57 |
| 5,604,812 | 2/1997 | Meyer ................ 381/68.2 |
| 5,609,616 | 3/1997 | Schulman et al. . |
| 5,624,376 | 4/1997 | Ball et al. . |
| 5,755,743 | 5/1998 | Volz et al. . |
| 5,788,711 | 8/1998 | Lehner et al. . |
| 5,814,095 | 9/1998 | Müller et al. . |
| 5,859,916 | 1/1999 | Ball et al. . |

FOREIGN PATENT DOCUMENTS

| | | |
|---|---|---|
| WO 97/18689 | 5/1997 | (WO) . |
| WO 98/03035 | 1/1998 | (WO) . |
| WO 98/06237 | 2/1998 | (WO) . |
| WO 98/36711 | 8/1998 | (WO) . |
| WO 99/07436 | 2/1999 | (WO) . |
| WO 99/08475 | 2/1999 | (WO) . |
| WO 99/08481 | 2/1999 | (WO) . |

OTHER PUBLICATIONS

HNO 1998, 46:pp. 844–852, Springer–Verlag 1998, H.P. Zenner et al., Erste Implantationen Eines Vollständig Implantierbaren Elektronischen Hörsystems Bei Patienten Mit Innenohrschwerhörigkeit.

HNO 1998, 46: pp. 853–863, Springer–Verlag 1998, H. Leysieffer et al., Ein Vollständig Implantierbares Hörsystem Für Innenohrschwerhörige: Tica LZ 3001.

HNO 1997 45:pp. 816–827, Springer–Verlag 1997, H. Leysieffer et al., Ein Implantierbares Mikrofon Für Elektronische Hörimplantate.

Primary Examiner—Jeffrey R. Jastrzab
(74) Attorney, Agent, or Firm—Nixon Peabody LLP; David S. Safran

(57) ABSTRACT

A fully implantable hearing system for rehabilitation of a pure sensorineural hearing loss or combined conduction and inner ear hearing impairment, comprising at least one implantable sensor which generates an electrical audio signal, at least one signal processing and amplification unit in an audio-signal processing electronic hearing system path, at least one implantable electromechanical transducer and a unit for supplying power for the implant system. The hearing system is furthermore provided with an implant-side measurement unit which acquires the electrical sensor signal (s) electronically by measurement engineering and electronically conditions the signal(s). Also, a wireless telemetry unit is provided on the implant side which transfers the electronically conditioned sensor signal(s) to the outside to an external display and/or evaluation unit.

24 Claims, 4 Drawing Sheets

FULLY IMPLANTABLE HEARING SYSTEM WITH TELEMETRIC SENSOR TESTING

BACKGROUND OF THE INVENTION

1. Field of the Invention

The present invention relates to implantable hearing systems for rehabilitation of pure sensorineural hearing losses, or combined conduction and inner ear hearing impairments. In particular, the invention relates to such hearing system in which as implantable sensor delivers an electrical audio signal which is processed by an implanted processor and delivered to an to implantable electromechanical transducer which acts on the middle or inner ear.

2. Description of Related Art

Fully implantable hearing systems for rehabilitation of a pure sensorineural hearing loss, or combined conduction and inner ear hearing impairment, with mechanical stimulation of the damaged ear will soon be available on the market. Examples of these systems are disclosed in the journal HNO 46:844–852, 10-1998, H. P. Zenner et al., "Initial implantations of a completely implantable electronic hearing system in patients with sensorineural hearing loss"; U.S. Pat. Nos. 5,277,694; 5,788,711; 5,814,095; 5,554,096 and U.S. Pat. No. 5,624,376. These hearing systems have basically four function units, specifically a sensor (microphone) which converts the incident airborne sound into an electrical signal, an electronic signal processing and amplification unit, an electromechanical transducer which converts the amplified and preprocessed sensor signals into mechanical vibrations and sends them via suitable coupling mechanisms to the damaged middle and/or inner ear, and an electrical power supply system which supplies these modules. Furthermore, a unit may be provided which supplies electrical recharging energy to the implant, when the implant-side power supply unit contains a rechargeable (secondary) battery, for example as shown in U.S. Pat. No. 5,279,292. A telemetry unit may also be provided with which patient-specific audiological data can be bidirectionally transmitted wirelessly or programmed in the implant and thus permanently stored as disclosed in the journal HNO 46:853–863, 10-1998, H. Leysieffer et al., "A completely implantable hearing system for inner ear hearing handicapped: TICA LZ 3001".

Especially in fully implantable systems is the visibility of the system not an issue. As a result, in addition to the advantages of high sound quality, the open auditory canal and full suitability for everyday use, high future patient acceptance can be assumed. Basically, in these implantable systems, the output signal is a mechanical vibratory stimulus which directly excites the middle ear or inner ear. The coupling of the mechanical excitation which is produced by an electromechanical transducer takes place by direct mechanical connection of the vibrating transducer element to the ossicle chain or an ossicle of the middle ear or to the inner ear, e.g. commonly owned co-pending U.S. patent application Ser. No. 09/042,805 filed Mar. 17, 1998, or by force coupling via an air gap in electromagnetic transducers, for example.

The airborne sound signal is converted into an electrical signal which can be further processed and amplified in an electronic unit and then conditioned, by a special sensor (microphone) which is positioned subcutaneously in fully implantable hearing systems, i.e. under the closed skin. The electrical signal triggers the implanted electromechanical transducer for middle ear or inner ear excitation. The area of the auditory canal, the eardrum itself or the malleus which has fused with the eardrum or other ossicle of the middle ear, has been selected to be acoustically and audiologically advantageous as the implantation site of the sensor. The sensor is basically a mechano-electrical converter with an input signal which is a mechanical vibration which results from the acoustic density wave of the incident airborne sound. These implantable, acoustic or mechano-electrical sensor systems are described in the scientific literature such as the journal HNO 45:816–827, 10-1997, H. Leysieffer et al., "An implantable microphone for electrical hearing implants" and in published U.S. Pat. No. 5,814,095, commonly-owned co-pending U.S. patent application Ser. No. 09/097,710 filed Jun. 16, 1998, U.S. Pat. Nos. 4,729,366, 4,850,962 and published PCT Application No. 98/36711, published PCT Application No. 98/06237, U.S. Pat. No. 5,859,916, published PCT Application Nos. 98/03035, 99/08481, 99/08475, 99/07436, 97/18689.

The function of this sound-converting sensor or microphone in a fully implantable hearing system is to convert the external, incident airborne sound into an electrical signal which can be sent to a subsequent electronic signal processing and amplification unit. Since in a full implant, for reasons of biostability and hygiene, it is fundamentally critical that no artificial and permanent body opening or skin opening be produced by which the sound to be converted can be supplied to a sensor or microphone, there is biologically active tissue between the sensor elements and the external, sound-carrying medium, i.e. air. This tissue can be the skin of the auditory canal for a microphone implanted subcutaneously in the posterior wall of the auditory canal, as discussed in the journal HNO 45:816–827, 10-1997, H. Leysieffer et al., "An implantable microphone for electronical hearing implants", U.S. Pat. No. 5,814,095 and the above-mentioned U.S. application Ser. No. 09/097,710. Alternatively, in the case of direct mechanical sensor coupling to the eardrum or the malleus in the tympanic cavity or in hermetically sealed housings in retroauricular, subcutaneous areas of the mastoid, it can be a bony or cartilaginous structure such as disclosed in U.S. Pat. No. 4,729,336, U.S. Pat. No. 4,850,962, published PCT Application No. 98/36711, published PCT Application No. 98/06237, U.S. Pat. No. 5,859,916, published PCT Application Nos. 98/03035, 99/08481, 99/08475, 99/07436, 97/18689. In these types of sensor or microphone placements, which is always done subcutaneously, the uncertainty of a long-term stable, reliable coupling exists since the placement can be affected by necroses formation, temporary or permanent seromae, tissue regeneration (for example, connective tissue), air pressure changes in hermetically tight pressure converter sensors and other external and internal actions. Even if these influences can be minimized by suitable sensor design, the interindividual anatomy, which can likewise affect the sensor transfer function, remains as a variable factor.

Exact knowledge of this sensor transfer function, i.e. the frequency-dependent acoustic pressure transfer factor, which quantitatively describes the conversion of acoustic pressure into a proportional electrical signal, is of great importance for individual adaptation of the audiological hearing system parameters, for example the frequency-dependent amplification. Intraoperatively, an a priori estimate of sensor function data can be determined using suitable measurement methods, but this data is certainly not identical to those of the healed, postoperative state. In particular, measurements of the acoustic directional characteristic of the sensor in the implanted state are of great interest; these measurements are basically impossible intraoperatively.

SUMMARY OF THE INVENTION

The object of this invention is therefore to devise a fully implantable hearing system which makes it possible to objectively measure, on an individual basis, the sensor transfer function in the implanted and postoperative healed state.

This and other objects are achieved by a fully implantable hearing system for rehabilitation of a pure sensorineural hearing loss or combined conduction and inner ear hearing impairment, comprising at least one implantable sensor which delivers an electrical audio signal, at least one signal processing and amplification unit in an audio-signal processing electronic hearing system path, at least one implantable electromechanical transducer and a unit for power supply of the implant system. Specifically, this object is achieved by the present invention in that the hearing system on the implant side is equipped with a measurement unit which acquires the electrical sensor signal or signals electronically by measurement engineering and electronically conditions the signal or signals. The system also includes a wireless telemetry unit which is likewise located on the implant side and which transfers the electronically conditioned sensor signal or signals, which has or have been acquired by measurement engineering, to the outside to an external display and/or evaluation unit.

The sensor signal which has been acquired by measurement can be evaluated externally. The implant-side measurement unit can likewise be provided with an evaluation unit in order to effect at least one preliminary evaluation on the implant side. For example, the implant-side evaluation unit can be a means for spectral analysis of the sensor signal such as a Fast Fourier Transform (FFT) with result data which is transferred, after the completed measurement, "offline" via the telemetry unit to an external display and evaluation unit. These approaches can be implemented especially advantageously when audio signal processing of the fully implanted hearing system is based on digital signal processing, since in this implementation the electrical sensor signal is present in digitized form directly or after analog preamplification. By a digital signal processor which is likewise present, these evaluation procedures, which are for example spectral, can be easily implemented by software algorithms without additional, implant-side hardware costs. The implant side measurement unit and the external evaluation unit can be designed especially for determining the frequency-dependent acoustic pressure transfer factor and/or the acoustic directional characteristic of the sensor in the implanted state. The hearing system can furthermore be provided with an electronic unit for selecting and/or changing the measurement functions of the implant-side measurement unit.

The hearing system can be designed for transfer of the measurement data, made available by the measurement unit, in real time. The data of the sensor transfer function, for example, can be read out later as required, and time staggered, when the corresponding storage media is on the implant-side.

The electronic signal processing and amplification unit has an amplifier downstream of the sensor, an audiological signal processing stage supplied with the output signal of the amplifier, and a driver amplifier upstream of the electromechanical output transducer. It is preferably provided with a digital signal processor with an upstream analog-digital converter and a downstream digital-analog converter.

Within the framework of the invention on the implant side, an independent measurement unit may be provided. The signal processor can however also form the implant-side measurement unit together with the upstream analog to digital converter.

The implantable electromechanical output transducer is preferably a transducer as disclosed in U.S. Pat. No. 5,277,694, i.e. a transducer in which one wall of the transducer housing is made as a vibratory membrane which together with a piezoelectric ceramic disk applied to the membrane inside represents an electromechanically active heteromorphic composite element.

Another transducer design suitable for these purposes is described in commonly-owned co-pending U.S. patent application Ser. No. 09/275,872. It is a transducer arrangement for partially or fully implantable hearing aids for direct mechanical excitation of the middle ear or inner ear. This arrangement is provided with a housing which can be fixed at the implantation site with respect to the skull, and a mechanically stiff coupling element which can move relative to the housing. The housing contains an electromechanical transducer with which the coupling element can be caused to vibrate. These vibrations are transmitted to the middle ear ossicle or directly to the inner ear after completed implantation of the transducer arrangement. The electromechanical transducer is made as an electromagnet arrangement including a component such as a ring coil which is fixed relative to the transducer housing, and a vibratory component, preferably in the form of a permanent magnetic pin, which dips into the center opening of the ring coil and which is connected to the coupling element such that the vibrations of the vibratory component are transmitted to the coupling element.

A transducer of the type described in commonly-owned, co-pending U.S. patent application Ser. No. 09/311,563 filed May 14, 1999 is also advantageous. It is a transducer for partially or fully implantable hearing aids for direct mechanical excitation of the middle ear or inner ear which is provided with a housing which can be fixed at the implantation site. The transducer also includes a mechanically stiff coupling element which can move relative to the housing wherein the housing contains a piezoelectric element with which the coupling element can be caused to vibrate. These vibrations are transmitted to the middle ear ossicle or directly to the inner ear after completed implantation of the transducer. An electromagnet arrangement is also provided in the housing which includes a component fixed relative to the housing and a vibratory component connected to the coupling element such that the vibrations of the vibratory component are transmitted to the coupling element. This transducer has the advantage that the frequency response of the transducer can be improved both compared to purely piezoelectric and also purely electromagnetic systems so that an adequate hearing impression at a sufficient loudness level is achieved. In particular, a largely flat frequency response of the deflection of the coupling element can be implemented in a wide frequency band at a sufficiently high stimulation level and low power consumption.

The digital to analog converter and the driver amplifier can be combined in one module. Also, the signal processor is preferably equipped with a data storage area for storing the patient-specific, audiological adaptation parameters and/or software algorithms for evaluating the electrical sensor signal.

A microcontroller, which includes a data storage area for storing patient-specific, audiological adaptation parameters and/or the parameters for the measurement function of the implant-side unit, may be provided to control at least one part, and preferably all, of the signal processing and/or generating stages. The signal processor, however, can also be designed itself for controlling at least one part, and preferably all, of the signal processing and/or generating stages. The telemetry unit can also be designed for data input into the data store and can communicate by wire or wirelessly with an external programming system.

If the hearing aid is made fully implantable, preferably the signal processing and amplification unit which is in the electronic hearing system path, the implant-side measurement unit and the telemetry unit are housed as the electronic module, together with the power supply unit, in a hermetically tight and biocompatible implant housing. In this case, the electronic module is advantageously connected via an implant line to a sensor, which can be implanted subcutaneously in the posterior wall of the auditory canal, and via an implantable line to the electromechanical output transducer. This connection can be made permanent or detachable. For a detachable connection, U.S. Pat. No. 5,755,743 discloses a preferred a plug-in connection. One such connection arrangement has at least one first contact, at least one second contact supported on an elastic body and a sealing mechanism for causing the face of the first contact to engage the face of the second contact. The first contact is surrounded by at least one sealing crosspiece which is pressed into the elastic body when the contacts engage and seals the contacts to the outside.

The output transducer can be coupled, preferably via a coupling element, to an ossicle of the middle ear chain for transmission of the output-side mechanical transducer vibrations. Specifically, the approaches of the type described in U.S. Pat. No. 5,277,694 and commonly-owned co-pending U.S. patent application Ser. No. 09/042,805 are suitable for this purpose. Advantageously an actively vibratory part of the output transducer can be securely and mechanically joined to a connecting rod which is coupled via a coupling element to one part of the ossicle chain. To adjust the relative location of the connecting rod and coupling element, and to fix these elements in the set relative position, the coupling element is preferably sleeve-shaped at least in the fixing area and plastically cold-deformed by means of a crimping tool. Also, the connecting rod is bar-shaped at least in the fixing area and provided with a rough surface. Under the influence of the crimping force applied with the crimping tool, the connecting rod cannot be plastically cold-deformed. In the fixed state, the sleeve-shaped part of the coupling element is attached permanently and without play on the bar-shaped part of the connecting rod after being deformed by cold flow by the crimping force. The end of the connecting rod away from the output transducer however can also be inserted into a hole of one part of the ossicle chain and fixed there. Furthermore, the output transducer can also be designed to be coupled via an air gap to the ossicle chain or the inner ear, as is described in particular in U.S. Pat. No. 5,015,225.

A fully implantable hearing aid, in another embodiment of the invention, includes an external system for transcutaneous transfer of patient-specific hearing system data and programming data for the implant-side measurement unit to the implant-side telemetry unit.

As the power supply unit, a primary battery or a secondary, rechargeable element, i.e. a rechargeable battery, can be used. In the latter case, the telemetry unit is also preferably a power receiving circuit for implant-side availability of recharging energy for the power supply unit, while the external system is built as a charger. In particular, a charging system of the type disclosed in U.S. Pat. No. 5,279,292 or arrangements as are described in commonly-owned, co-pending U.S. patent application Ser. No. 09/311,565 filed May 14, 1999 and in commonly-owned, co-pending U.S. patent application Ser. No. 09/311,566 filed May 14, 1999, are suitable for this purpose.

A portable remote control unit for setting or changing the hearing aid and audiometry functions may also be provided.

In the following, advantageous embodiments of the invention are explained using the drawings.

DETAILED DESCRIPTION OF THE INVENTION

Figure 1:
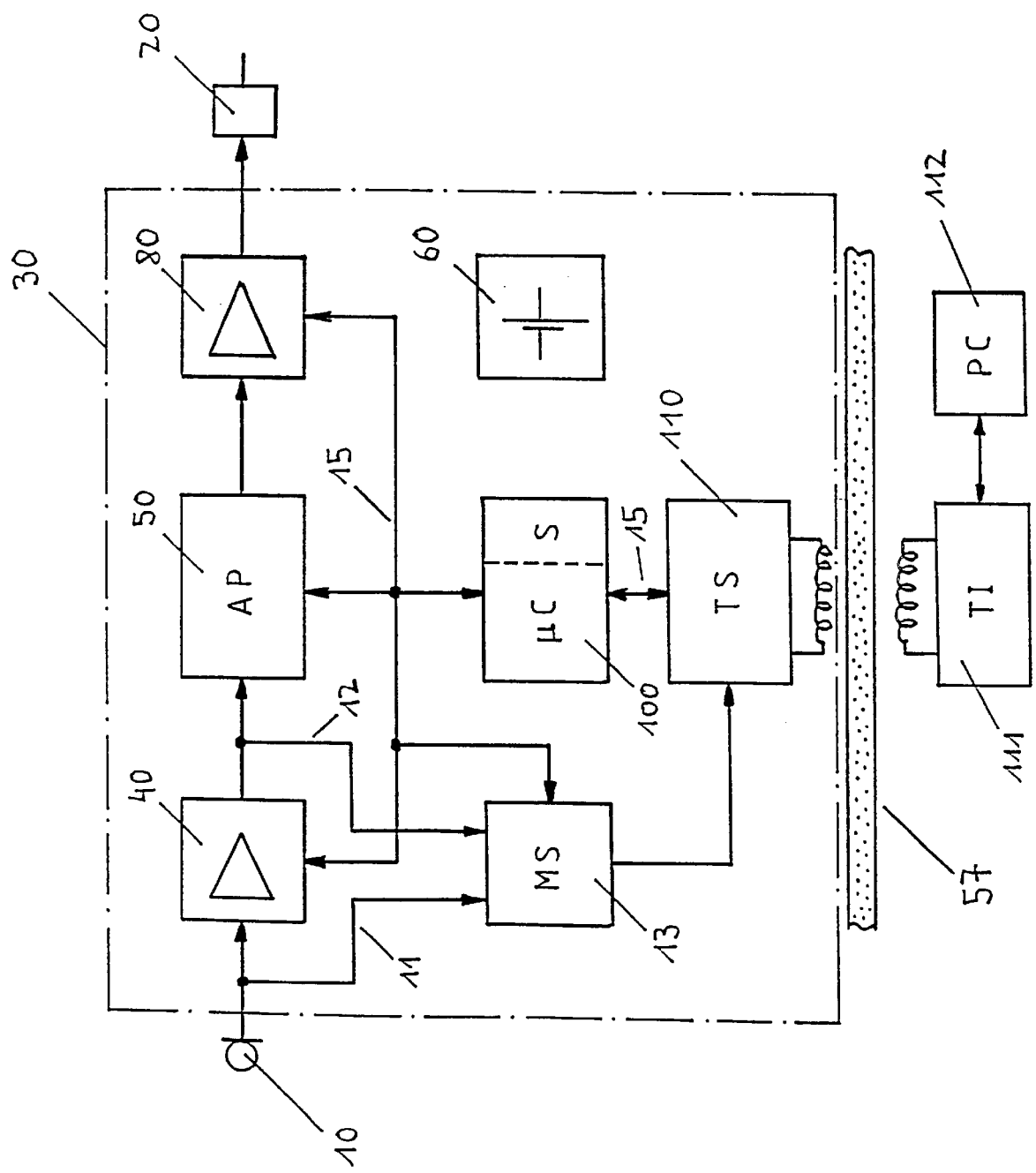
FIG. 1 shows a block diagram of a fully implantable hearing system as claimed in the invention with telemetric sensor testing.

The hearing system as shown in FIG. 1 includes a sensor 10 (microphone) which receives the external acoustic signal and converts the signal into an electrical signal. This sensor signal travels to an implant module 30 wherein the electrical sensor signal is preamplified by an amplifier 40. This preamplified signal is further processed in an audiological signal processing stage 50 (AP: "Audio Processor"). This stage can contain all known components conventional in modem hearing aids, such as filter stages, automatic gain controls, interference signal suppression means, and so forth. This processed signal is sent to a driver amplifier 80 which triggers an electromechanical transducer 20. The transducer 20 stimulates the impaired inner ear by direct mechanical coupling to a middle ear ossicle or via an air gap coupling for implantable converters which are for example electromagnetic. The signal processing components 40, 50, 80 are controlled by a microcontroller 100 ($\mu$C) with the associated data storage (S) via a unidirectional or bidirectional data bus 15. In the storage area S, patient-specific audiological adaptation parameters can be filed. This individual programmable data is sent to the controller 100 via the data bus 15 by a telemetry unit 110 (T). This telemetry unit 110 communicates wirelessly through the closed skin shown at 57, for example as shown in FIG. 1, via an inductive coil coupling, and bidirectionally with an external telemetry interface 111 (T1). The telemetry interface 111 is in bidirectional communication with a display and/or evaluation unit 112 which can advantageously be a computer (PC) with the corresponding processing and display software.

In addition to the above described modules necessary for a hearing aid function, the implant module 30 contains an electronic measurement system 13 (MS) to which the electrical sensor signal is supplied via a line 11 directly or via a line 12 after preamplification by the amplifier 40. The measurement system 13 prepares the sensor information and relays it to the telemetry system 110 so that the sensor data can be transmitted to the outside and to the display unit 112 via the telemetry interface 111. The measurement system 13 is likewise controlled via the data bus 15 of the implant controller 100 so that the sensor signal on the line 11, or the preamplified signal on line 12, can be selected as required.

The measurement system 13 may contain analog, digital and mixed analog and digital measuring transducers, evaluation circuits and modulation means which are accordingly selected and optimized depending on the type of telemetry system 110. The parameters of the measurement functions of the measurement system 13 can likewise be selected or changed via the data bus 15 by the controller 100. The request for a measurement function takes place via control commands of the external unit 112 via the telemetry interface 111. These control commands trigger the corresponding actions of the implant-side controller 100.

All electronic components of the system are supplied with electrical operating power by a primary or rechargeable secondary battery 60. The sensor 10 and the electronic transducer 20 can be connected to the implant module 30 permanently or alternatively via implantable plug-in connections.

Figure 2:
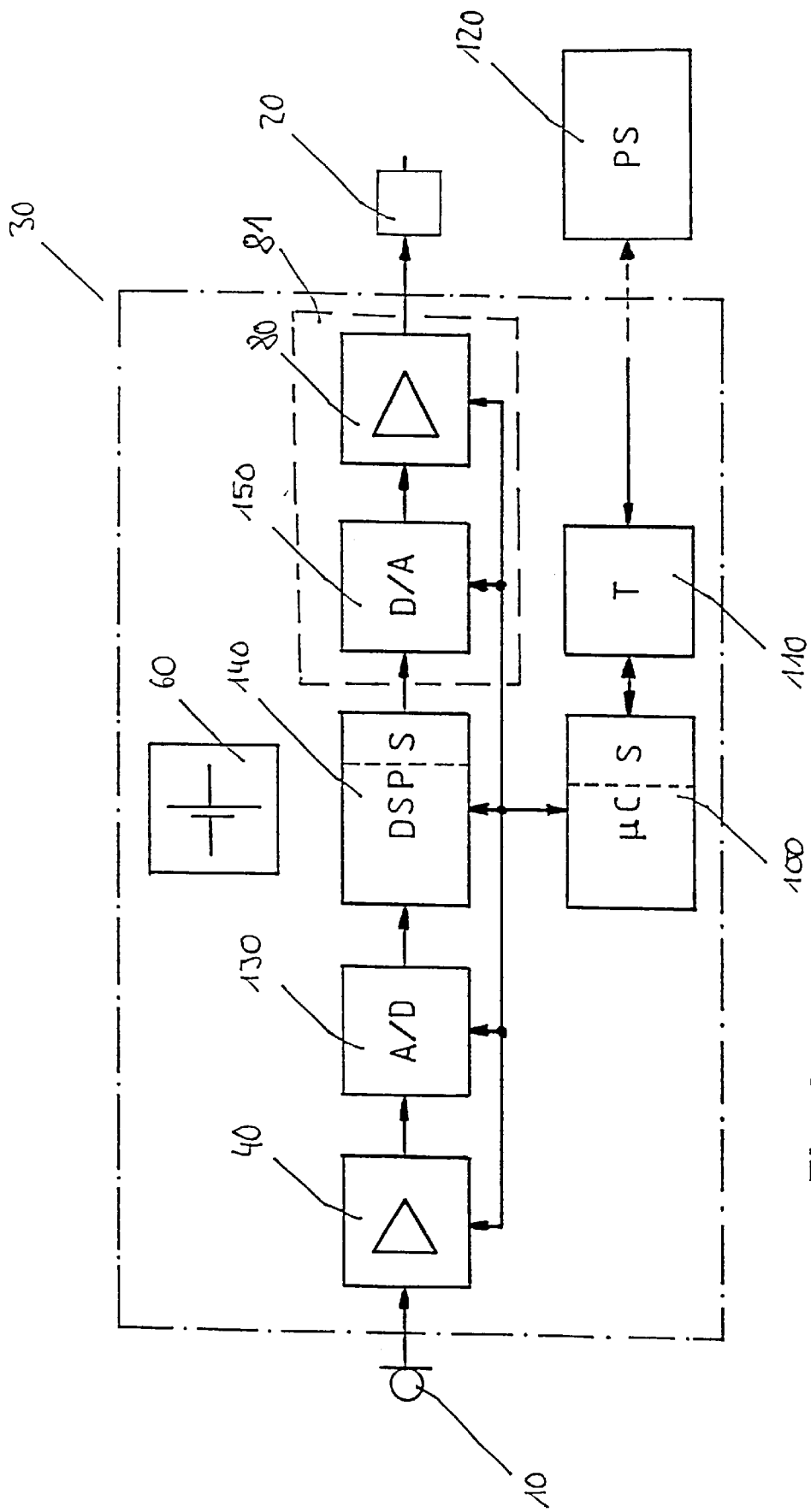
FIGS. 2 and 3 shows block diagrams of modified embodiments of the fully implantable hearing system.

FIG. 2 illustrates another embodiment of the electronic implant module 30. The signal of the sensor 10 is preamplified in the amplifier 40 and, by means of an analog-digital converter 130 (A/D), is converted into a digital signal which is sent to a digital signal processor 140 (DSP) having a data storage area S. The digital output signal of the signal processor 140 is converted back into an analog signal in the digital to analog converter 150 (D/A) and then supplied to the electromechanical transducer 20 via the driver amplifier 80.

The analog to digital converter 130 and the signal processor 140 assume two tasks in this case: on the one hand, as is conventional in fully digital hearing aids, the audio signal is conventionally conditioned and processed according to the described signal processing methods for rehabilitation of inner ear impairment. On the other hand, the analog to digital converter 130 and the signal processor 140 comprise the measurement system 13 according to FIG. 1. Direct access to the sensor signal 11 as in FIG. 1 is, however, not possible in the present embodiment since the sensor signal must be preamplified before A/D conversion and must be low-pass filtered. The necessary low-pass can be implemented in the preamplifier 40.

The signal processor 140, in one sample application, transfers the sensor signals, converted from analog to digital, to the implant controller 100 which transfers the signals to the external display and evaluation unit via the telemetry system 110. FIG. 2 shows the telemetry interface 111 and the display and evaluation unit 112 from FIG. 1 in combination as the external programming system 120 (PS). With a corresponding design of the individual components, telemetric transmission of sensor data can take place so quickly that a quasi-real time measurement is taken. Thus, for example, measurements of the spatial directional effect of the sensor 10 implanted in the patient can be taken. In another sample application, the signal processor 140 may contain software algorithms which execute an evaluation of the electrical sensor signal. These evaluations can, for example, be time averagings in order to improve the signal-to-noise ratio of the sensor output for low level acoustic input signals. Furthermore, algorithms, such as a Fast Fourier Transform (FFT), can be implemented which enable spectral evaluation of the sensor signal for broadband acoustic input sounds (for example, broadband test noise or short clicks, e.g. acoustic Dirac pulses) in order to thus determine, for example, the frequency-dependent, acoustic attenuation properties of the biological medium placed between the airborne sound and the implant sensor. Furthermore, these spectral analyses also yield aspects or parameters of the sensor transfer function given by the patient anatomy which is always individually different (for example, geometrical aspects of the external auditory canal, head shape and the like) or by time-variant influences such as, for example, pathological changes of the middle ear (for example, otitis media). The results of these measurements within the implant can be filed as measurement data in the storage area S of the signal processor 140 and/or the storage area of the implant controller 100. The results are read out as necessary via the described telemetry system 110 and the external programming and evaluation systems 120.

The D/A converter 150 and the driver amplifier 80 can, as is shown in FIG. 2 by the block 81, be combined in one module. This is especially preferred in the case in which an electromagnetic system is used as the transducer 20 and the output signal of the signal processor 140 contains the signal information by pulse-width modulation so that the time integration necessary for conversion back into an analog signal is done directly by the transducer 20.

Figure 3:
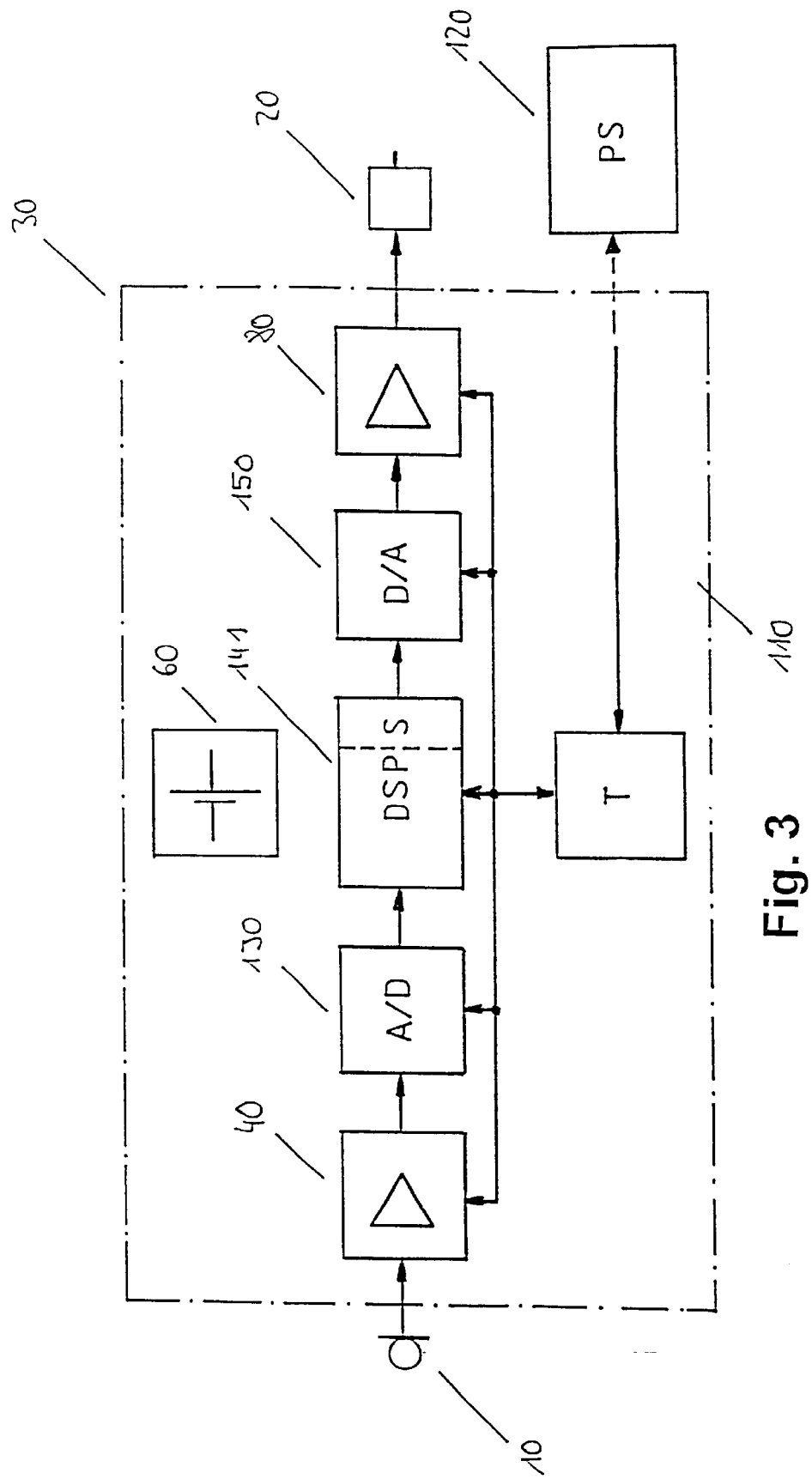

The embodiment as shown in FIG. 3 differs from that of FIG. 2 essentially only in that there is a signal processor 141 which also assumes the functions of the microcontroller 100 as shown in FIG. 2. In this case, the patient-specific data of audio signal processing and the above-described result data of the measurement system algorithm of the sensor signal are filed in the data storage area S of the signal processor 141.

Figure 4:
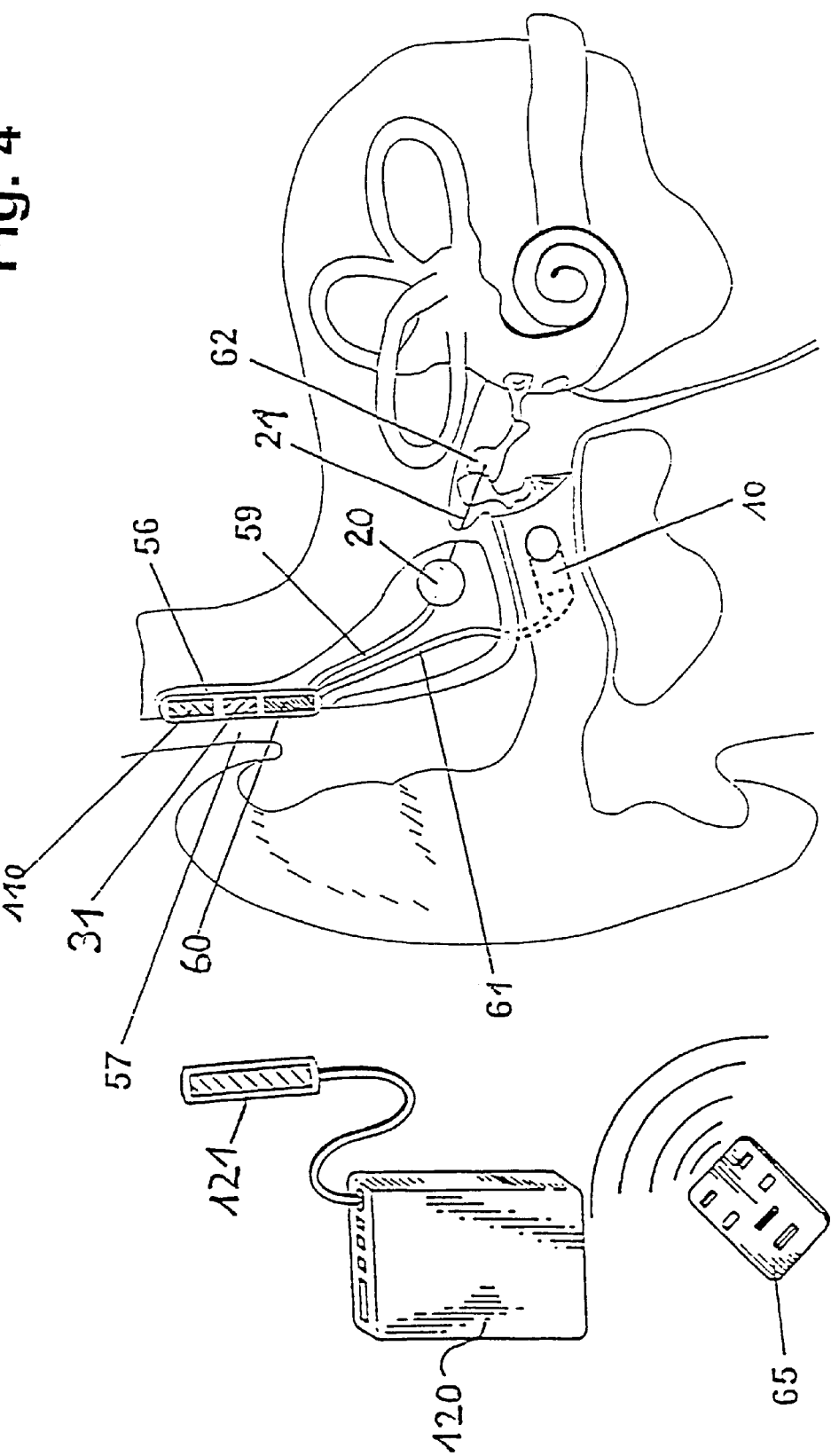
FIG. 4 shows a schematic of a fully implanted hearing system in the implanted state.

FIG. 4 shows one possible embodiment of the fully implantable hearing system with telemetric sensor testing as shown in FIG. 1, FIG. 2 or FIG. 3 in schematic form. A hermetically tight and biocompatible implant housing 56 holds an electronic module 31 (shown without the battery) which corresponds to the module 30 of FIGS. 1, 2, and 3 except for the absence of a battery. Furthermore, the housing 56 contains the battery 60 for electrical supply to the implant and the telemetry means 110. The sensor (microphone) 10 is subcutaneously implanted in the posterior wall of the auditory canal preferably in the manner disclosed in U.S. Pat. No. 5,814,095, or alternatively using the fixation element described in U.S. patent application Ser. No. 09/097,710. The sensor 10 picks up the sound and converts it into an electrical signal which is supplied via the implant line 61 to the electronic module 31 in the housing 56. The audiologically processed and amplified signal travels via the implantable line 59 to the electromechanical transducer 20. This transducer 20 in this example is shown as a directly coupled system, i.e. the output-side mechanical vibrations of the transducer 20 are coupled directly via a suitable coupling element 21 to an ossicle of the middle ear chain, i.e. to the anvil 62. Preferably, this takes place in the manner disclosed in U.S. Pat. Nos. 5,277,694 and 5,788,711. The coupled transducer vibrations travel via the ossicle chain to the inner ear and cause the corresponding auditory sensation.

Furthermore, FIG. 4 illustrates the external programming, display and evaluation system 120 with which, as described, the patient-specific hearing aid data are read and programmed transcutaneously and the sensor data, measured within the implant, is transferred. To do this, a transmitting and reading head 121 is used which is placed above the implant for bidirectional data transfer and transfers the data, for example, inductively. If the battery 60 in the implant housing 56 is a secondary, rechargeable element, the unit 110 can also be a power receiving circuit for implant-side availability of recharging energy. Then the external system 120, with the transmitting head 121, is a wireless charger which is portable. In this case, preferably there may be arrangements such as disclosed in U.S. Pat. No. 5,279,292 or as explained in U.S. patent application Ser. Nos. 09/311,565 and 09/311,566. Furthermore, a portable remote control unit 65 is shown with which the patient can adjust or change important hearing aid functions.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as are encompassed by the scope of the appended claims.

What is claimed is:

1. A fully implantable hearing system for rehabilitation of at least one of a pure sensorineural hearing loss and a combined conduction and inner ear hearing impairment, comprising:

at least one implantable sensor which generates an electrical audio signal;

at least one signal processing and amplification unit adapted to be positioned in an audio-signal processing electronic hearing system path;

at least one implantable electromechanical output transducer;

a unit for supplying power for the implant system;

an implant-side measurement unit adapted to acquire the electrical audio signal electronically by measurement engineering and electronically condition the sensor signal; and a wireless telemetry unit located on an implant side and adapted to transfer the electronically conditioned sensor signal to at least one of an external display and an external evaluation unit.

2. The hearing system of claim 1, wherein the implant-side measurement unit contains an internal evaluation unit.

3. The hearing system of claim 1, further comprising an implant side measurement unit and an external evaluation unit; and wherein the implant side measurement unit and the external evaluation unit are adapted to determine at least one of a frequency-dependent acoustic pressure transfer factor and an acoustic directional characteristic of the at least one sensor in an implanted state.

4. The hearing system of claim 1, further including an electronic unit for at least one of selecting and changing measurement functions of the implant-side measurement unit.

5. The hearing system of claim 1, wherein the telemetry unit is adapted to transfer measurement data made available by the measurement unit in real time.

6. The hearing system of claim 1, wherein the hearing system is designed for implant-side storage of measurement data made available by the measurement unit, wherein the stored measurement data can be read out in a time-staggered manner as required via the telemetry unit.

7. The hearing system of claim 1, wherein the electronic signal processing and amplification unit includes an amplifier downstream of the at least one sensor, an audiological signal processing stage for receiving the output signal of the amplifier, and a driver amplifier upstream of the at least one electromechanical output transducer.

8. The hearing system of claim 1, wherein the electronic signal processing and amplification unit includes a digital signal processor, an upstream analog-digital converter and a downstream digital-analog converter.

9. The hearing system of claim 8, wherein the digital signal processor together with the upstream analog to digital converter forms the implant-side measurement unit.

10. The hearing system of claims 9, wherein the digital to analog converter downstream of the signal processor and the driver amplifier are combined in one module.

11. The hearing system of claim 8, wherein the signal processor includes a data storage area for storing at least one of patient-specific, audiological adaptation parameters and software algorithms for evaluation of the sensor signal.

12. The hearing system of claim 8, wherein at least one component of the signal processing and amplification unit is controlled by a microcontroller.

13. The hearing system of claim 12, wherein the microcontroller includes a data storage area for storing at least one of patient-specific, audiological adaptation parameters and parameters for the measurement function of the implant-side measurement unit.

14. The hearing system of claim 8, wherein the digital signal processor is designed to control at least one component of the signal processing and amplification unit.

15. The hearing system of claim 11, wherein said telemetry unit functions to input data into the data storage area.

16. The hearing system of claim 15, further including an external programming system which communicates wirelessly with the telemetry unit.

17. The hearing system of claim 1, wherein the system is made fully implantable, the signal processing and amplification unit, the implant-side measurement unit for generating and feeding the signals necessary for the audiometry function and the telemetry unit being housed together with the power supply unit, in a hermetically tight and biocompatible implant housing to form an electronic module.

18. The hearing system of claim 17, wherein the implantable sensor is a microphone adapted to be implanted subcutaneously in the posterior wall of the auditory canal, said electronic module being connected via an implant line to said microphone.

19. The hearing system of claim 17, wherein the electronic module is connected via an implantable line to the at least one electromechanical output transducer.

20. The hearing system of claim 1, wherein the at least one electromechanical output transducer is adapted to be coupled via a coupling element to an ossicle of a middle ear chain for transmission of output-side mechanical transducer vibrations.

21. The hearing system of claim 1, wherein the at least one electromechanical output transducer is adapted to be coupled via an air gap to at least one of an ossicle chain and an inner ear.

22. The hearing system of claim 1, further including an external system for transcutaneous transfer of patient-specific hearing system and audiometry programming data to the implant-side telemetry unit.

23. The hearing system of claim 22, wherein the power supply unit is a secondary, rechargeable element, the telemetry unit including a power receiving circuit for implant-side availability of recharging energy for the power supply unit, the external system including a charger.

24. The hearing system of claim 1, characterized by a portable remote control unit for at least one of setting and changing hearing system and audiometry functions.

* * * * *